United States Patent [19]

Bonfiglio et al.

[11] Patent Number: 4,722,606
[45] Date of Patent: Feb. 2, 1988

[54] ANALYTICAL PHOTOMETER, IN PARTICULAR MULTI-CHANNEL, APPLIED TO A CENTRIFUGAL SYSTEM ADAPTED TO PERFORM PRACTICALLY SIMULTANEOUS DETERMINATION OF THE PRESENCE OF DIFFERENT SUBSTANCES IN A CERTAIN NUMBER OF SAMPLES

[75] Inventors: Paolo Bonfiglio, Bareggio; Claudio Calzi, Milan, both of Italy

[73] Assignee: Fisher Scientific Company, Pittsburgh, Pa.

[21] Appl. No.: 799,674

[22] Filed: Nov. 19, 1985

[30] Foreign Application Priority Data

Nov. 19, 1984 [IT] Italy ................................ 23647 A/84

[51] Int. Cl.⁴ .......................................... G01N 21/27
[52] U.S. Cl. .................................... 356/414; 356/427
[58] Field of Search ............... 356/414, 416, 418, 419, 356/432, 435, 436, 427

[56] References Cited

U.S. PATENT DOCUMENTS

| 3,599,002 | 8/1971 | Beutelspacher et al. | 356/432 |
| 3,807,874 | 4/1974 | Gropper | 356/427 |
| 4,312,593 | 1/1982 | Baker et al. | 356/414 |
| 4,329,062 | 11/1982 | Haar et al. | 356/414 |
| 4,406,547 | 9/1983 | Aihara | 356/414 |
| 4,482,251 | 11/1984 | Saylor | 356/414 |
| 4,652,137 | 3/1987 | Calzi | 356/414 |

FOREIGN PATENT DOCUMENTS

| 0081702 | 6/1983 | European Pat. Off. | 356/416 |
| 3500639 | 7/1985 | Fed. Rep. of Germany | 356/418 |
| 0031783 | 3/1977 | Japan | 356/414 |

OTHER PUBLICATIONS

Jauch, *J. Physc. F: Sci. Instrum.*, vol. 12, No. 12, Dec. 1979, pp. 1171–1175.

Primary Examiner—F. L. Evans
Attorney, Agent, or Firm—Alan M. Doernberg

[57] ABSTRACT

In an analytical photometer, in particular multi-channel, for the simultaneous analysis of a multiplicity of samples, the light source provided is a flash tube for producing light pulses in which a permanent preionization discharge is maintained and the light energy is derived by optical fibres to be sent to optical systems where the beam is divided into an analysis beam which travels through the sample and a reference beam, both finally delivered to photodetectors. Both the divided beams pass through identical filtering systems for selection of a narrow spectral band of relevance for analytical purposes.

8 Claims, 3 Drawing Figures

ANALYTICAL PHOTOMETER, IN PARTICULAR MULTI-CHANNEL, APPLIED TO A CENTRIFUGAL SYSTEM ADAPTED TO PERFORM PRACTICALLY SIMULTANEOUS DETERMINATION OF THE PRESENCE OF DIFFERENT SUBSTANCES IN A CERTAIN NUMBER OF SAMPLES

In general a double-beam spectrophotometer consists chiefly of a light source, a dispersive and/or selective system of narrow spectral bands useful for analytical pruposes, a device for dividing the light beam and photosensitive sensors for converting light energy to electrical energy.

A characterizing feature of said types of instrument is the light source, which should in theory have continuous emission with elevated and uniform intensity in the widest possible spectral range. In practice, however, this cannot be achieved, for the light sources available provide radiations having different intensities at different wavelengths.

The source most frequently employed for applications in the visible spectrum is the halogen lamp, which has however the disadvantage of providing negligible light energy in the ultraviolet.

In order to obviate this difficulty a second light source is usually employed in combination with the first, and is generally a deuterium lamp emitting in the ultraviolet.

The high degree of power-dissipation of incandescent halogen lamps in relation to the available light intensity, as well as the relatively limited service life of such lamps, are difficulties which have encouraged the use as a light source of flash tubes providing light pulses, which have the advantage of emitting radiation within a broad spectral range with elevated conversion of electrical to light energy and consequently with less energy dissipated as heat.

With said type of lamp a light source can be created with instantaneously emitted high light energy; moreover the lamp is of small bulk per se and also because it does not call for large surface area heat dissipators.

Nevertheless, the use in analytical spectrophotometer of flash tubes providing light pulses is for a variety of reasons not convenient. The intensity of the radiation emitted by the tube is not constant but varies appriciably in a random manner from one flash to the next, thus considerably altering the reproducibility of photometric measurements.

Such variations are due to various factors difficult to predict and control, as for example unstable relative temperatures of the gas and glass or quartz bulb, residual ionization and self-absorption, non-uniformity of gas pressure (e.g. xenon), etc.

In effect the path of the arc varies at random from one flash to the next, there is variation of the emitted light energy and of spectral energy distribution.

The known art has acknowledged these difficulties: an example of solution is advanced in U.S. Pat. No. 4,241,998, which proposes the use of a flash tube of clearly defined geometry so that the discharge is of a very brief duration and with maximal stability of spatial position from one flash to another. In said patent, a device conventionally named "stabilizing device" sends the light energy emitted by the flash tube within a clearly defined solid angle to a monochromator at the output of which the beam is divided into two beams, one being the reference beam and the other travelling, after appropriate filtration, through the sample for analysis.

A device of said known type is unsatisfactory in many applications: the reference beam emerging from the monochromator and sent to a photodiode provides a signal operating as general light source energy test which is insensitive to the spectral variation of the light energy that can be expected for successive flashes.

Moreover, the use of a lamp of somewhat inflexible geometry is obligatory. Overall, the device is of considerable bulk and thus not usable in spectrophotometric instruments providing for the simultaneous analysis of a multiplicity of samples, each requiring a single light beam.

One object of the present invention is to embody a spectrophotometer which as a light source employs a flash tube of conventional type but permitting highly reproducible measurements.

A further object of the invention is to embody a spectrophotometer in which a single light source, specifically a flash tube forms a multiplicity of light beams, each of which can be used for spectrophotometric analysis of a sample.

Another object of the invention, therefore, is to provide a device that is highly compact and that can be used in conjunction with a spectrophotometer of particular structure even when the simultaneous analysis of a multiplicity of samples is required.

The spectrophotometer according to the invention thus comprises a light source in the form of a flash tube, a first source of electrical energy for said tube having voltage and current values that create therein a substantially contiuous ionization discharge, a second source of pulsed electrical energy with voltage and current values which cause discharge of maximum power in the tube, at least one optical fibre disposed with one of its ends proximal to the tube in order to capture the light energy thereby emitted and the other end associated with an optical analysis unit in which a dividing device separates the beam emerging from the other of said light beams end of the fibre into two beams, each of which is sent to one of two optical filtering systems, which are identical, to obtain beams of filtered light having substantially the same spectral distribution, one of said light beams being sent through one of the optical filtering systems directly to a photosensitive transducer to obtain a reference signal and the other being sent through a sample for analysis and then the other of the optical filtering system to a photosensitive transducer to obtain an analysis signal.

The objects and essential characteristics of the invention will become more apparent from the following illustrative and not limiting form of embodiment thereof, with reference to the appended drawings in which.

Figure 1:
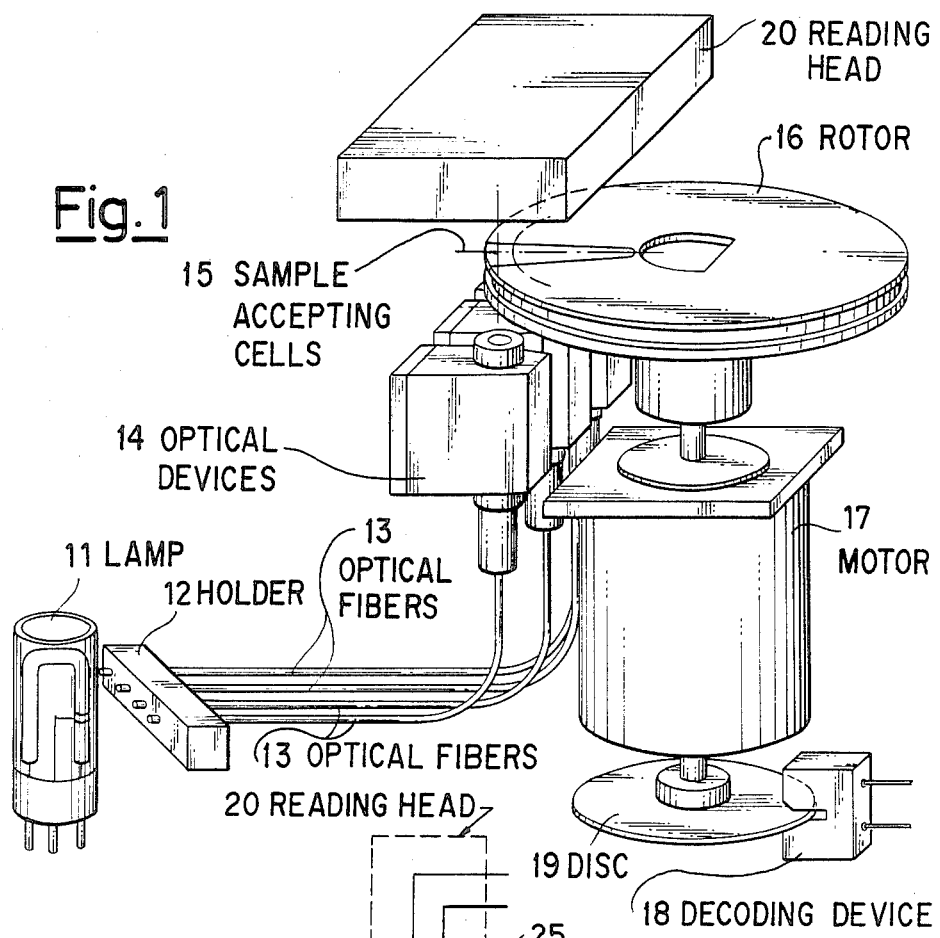
FIG. 1 is a schematic perspective view of the essential components of the photometer according to the invention.

As FIG. 1 shows, the spectrophotometer comprises a flash tube 11 in front of which is a holder 12 supporting the ends of a plurality of optical fibres 13; the holder 12 is restrained to the fixed structure (not illustrated) of the instrument in an adjustable manner so that it can be positioned on a manner that said fibres are disposed to intercept the maximum light signal through the agency of their ends.

Each of said optical fibres 13 leads to optical devices indicated overall by 14.

Said optical devices 14 are disposed proximally to sample-accepting cells 15 formed in a rotor 16, rotated by a motor 17. The angular position of the motor, and thus of the rotor 16, is sensed by a decoding device 18 associated with a disc 19 solid with the shaft of the motor 17 and provided with position detecting means read by the decoding device 18, according to one of the known forms of embodiment of the art.

Each optical device 14 is also associated with reading heads indicated overall by 20.

Figure 2:
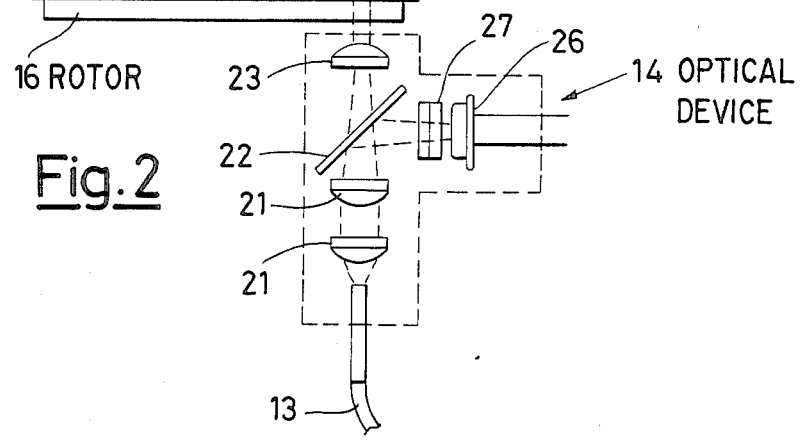
FIG. 2 is an exploded schematic view of a component of the photometer of FIG. 1.

FIG. 2 shows in greater detail one of the optical devices 14 and the components directly cooperating therewith.

The fibre 13 leads to the optical device 14 and the light beam emerging from its end is sent to an optical condenser 21, then to a separator 22 which divides said beam into a first measuring beam which travels through the collimator 23 by which it is focussed to reach the sample in the cell 15 of the rotor and, through it, to pass through the filtering system 24 and reach the photodetecting unit 25.

The second divided beam is a reference beam, and is sent to a photodetecting unit 26 through a filtering system 27 wholly identical with the system 24.

Figure 3:
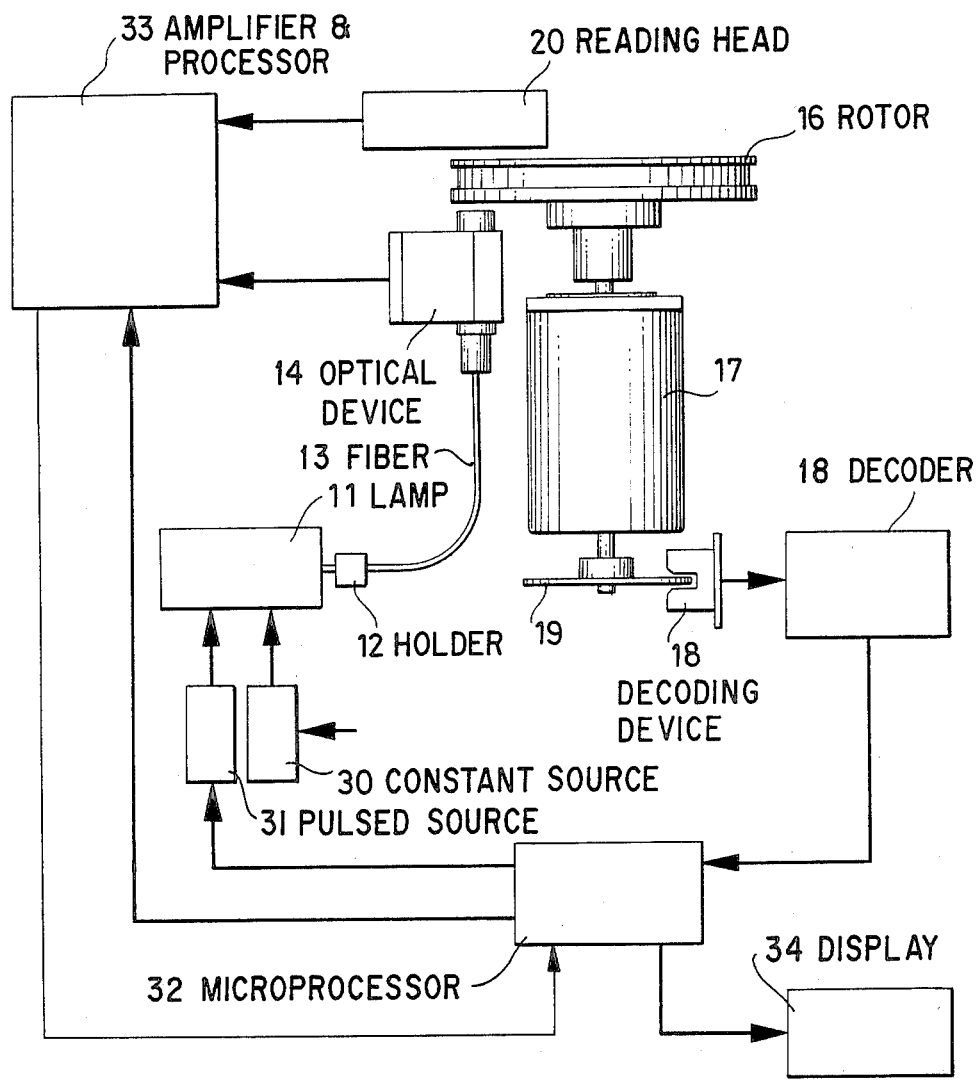
FIG. 3 is a general schematic of the instrument.

FIG. 3 is a general schematic of the photometer according to the invention, referred to its essential components.

The lamp 11 is supplied by a source 30 which, with controlled voltage and current, maintains in it a permanent preionization discharge, which is preferably established with activation of a conventional starter circuit.

A source 31 generates a pulsed power supply for instantaneous discharges in the lamp 11.

Activation of the source 31 is operated by a microprocessor unit 32 which receives a synchronism signal from a decoder 18a which transmits in electrical form the reading of decoding device 18; the microprocessor 32 also pilots the data acquisition on the reference beam from the optical device 14 and on the analysis beam from the reading head 20, by the amplification and processing unit 33; the unit 33 sends the signals to the microprocessor 32 which visualizes the analytical data at display 34.

No detailed description is herein given of the units 33 and 32 which synchronize the flashes of the flash tube 11 with the passage of the samples proximally to each of the optical devices 14 and simultaneously derives the signal from the corresponding photodetecting unit housed in 20, in that they can be per se embodied in different ways according to the knowledge common to persons skilled in the art.

The operating mode of the instrument described is as follows: the source 30 maintains in the flash tube 11 by means of controlled voltage and current a preionizing discharge of extremely low light intensity, which follows a pre-determined and spatially considerably stable path within the tube.

The flash tube is of a type which is available on the market, for example a low pressure xenon tube, since the geometry of the tube and thus the linear or curved nature of the discharge, the disposition of the electrodes or other particular characteristics of the flash tube are not critical factors.

When the source 31 sends a current pulse for the discharge of power, such discharge has been seen to tend markedly to follow the path of the permanent preionization discharge, with the result that it has a relatively stable path in space.

The optical fibre holder 12 can consequently be disposed in a defined position with respect to the power discharge path, specifically so that the fibre or fibres supported therein may capture an elevated and appreciably constant portion of light energy.

Each fibre 13 is advantageously of single-mode type, so as to obviate interference between the beams emerging from the single threads of multi-mode fibres. The presence of single-mode fibres of elevated length makes it conjointly possible to render more uniform the light output radiation with respect to input light radiation; it also permits the most rational disposition of the light source, separated from the sample-accepting portion of the spectrophotometer, which portion has its own specific size and shape requirements.

Transmission by optical fibres in practice enables an elementary source to be obtained, or a plurality of elementary sources consisting of the beams emergng from the ends of the fibres associated with each of the optical devices 14, which have very small dimensions and can thus be disposed proximally to the single samples for analysis in the most convenient manner.

The instrument of the invention is therefore adapted to be used in photometers for the simultaneous analysis of a multiplicity of samples of the particular type for example described in the Italian patent application 20 560 A/83 in the name of the present applicant.

The possibility of using lamps normally available on the market which have a relatively long discharge path in a rectilinear or curved tube permits the ready disposition in a suitable position of any desired number of unput ends of optical fibres, each connected to an optical device 14 for the analysis of a sample.

It should be noted that the identical nature of the filtration effected in the filtering systems 24 and 29 on the measuring and reference beams allows homogeneous signals to be obtained from the photodetecting units, in that they are equally sensitive both to the changes in light energy of each single flash and to any variation in the spectral distribution of light energy.

The identical filters in effect select the narrow spectral band radiation of both beams coincident with the wavelength of analytical pertinence, acting as interference filters with transmittance peak coincident with the wavelength called for by the analysis.

The above description of a form of embodiment is not limiting in respect to the structural and operating characteristics of the instrument according to the invention, in that it intends solely to explain how the principles on which the present invention is based may find practical application.

Numerous embodiment variants can therefore be made thereto by persons skilled in the art in the light of the specific requirements of each instrument.

We claim:

1. An analytical spectrophotometer for analyzing a sample comprising:
   (a) a flash tube for emitting a beam of light,
   (b) a first source of electrical energy for the flash tube which supplies voltage and current values to the flash tube sufficient to form a substantially continuous ionization discharge from the flash tube, (c) a second source of electrical energy which, when energized, supplies voltage and current values to the flash tube sufficient to cause the flash tube to emit a pulse of light of maximal power,
(d) at least one beam splitting device,
(e) at least one optical fiber having a first end positioned relative to the flash tube to capture light energy emitted by the flash tube and having a second end positioned relative to a beam splitting device for the beam splitting device to separate the beam of light emerging from the second end into a first split beam and a second split beam,
(f) a first optical filter positioned for the first split beam to pass through the first optical filter,
(g) a second optical filter having the same spectral characteristics as the first optical filter positioned for the second split beam to pass through the second filter,
(h) a reference photosensitive transducer positioned to receive the first split beam after the first split beam has past through the first optical filter,
(i) an analysis photosensitive transducer positioned to receive the second split beam after the second split beam has passed through a sample and through the second optical filter.

2. A spectrophotometer according to claim 1 comprising a plurality of optical fibers, each having a second end positioned relative to a separate beam splitting device and producing a separate second split beam which passes through a separate sample and second optical filter to a separate analysis photosensitive transducer.

3. A spectrophotometer according to claim 1 further comprising a centrifugal rotor having circumferentially separated sample holding cells and means for rotating the centrifugal rotor into positions in which each cell is position between a beam splitting device and a second optical filter in the path of a second split beam.

4. A spectrophotometer according to claim 3 further comprising a sensor of angular position for obtaining a signal of position for each single sample in the path of a second split beam, a microprocessor operated by the position sensor signal and controlling the activation of the second energy source to produce in the flash tube a discharge of maximal power when each sample is in the path of a second split beam and also controlling the derivation of the signals of the photosensitive transducers of the optical unit to obtain an analysis signal.

5. A spectrophotometer according to claim 4 wherein a plurality of beam splitting devices, each positioned at a second end of an optical fiber, are circumferentially distributed relative to the rotor and to a correspoding plurality of second optical filter and analysis photosensitive transducers such that a corresponding plurality of sample holding cells are each in the path of a second split beam.

6. A spectrophotometer according to claim 1 wherein said flash tube is of a low pressure xenon type.

7. A spectrophotometer according to claim 2 wherein the first ends of the fibers proximal to the flash tube are received in a position-wise adjustable holder in order to dispose said first ends to capture the radiations emitted by the tube in a solid angle in which the intensity of radiation is maximal.

8. A spectrophotometer according to claim 1 wherein the at least one optical fiber is of single-mode type.

* * * * *